(12) United States Patent
Terrisse et al.

(10) Patent No.: US 10,709,653 B2
(45) Date of Patent: Jul. 14, 2020

(54) COSMETIC COMPOSITIONS COMPRISING SPICULISPORIC ACID AND AT LEAST ONE SULFATE AND/OR SULFONATE SURFACTANT

(71) Applicant: L'OREAL, Paris (FR)

(72) Inventors: Isabelle Terrisse, Vitry sur Seine (FR); Caroline Sirichandra, Joinville le Pont (FR)

(73) Assignee: L'OREAL, Paris (FR)

( * ) Notice: Subject to any disclaimer, the term of this patent is extended or adjusted under 35 U.S.C. 154(b) by 16 days.

(21) Appl. No.: 15/034,114

(22) PCT Filed: Nov. 7, 2014

(86) PCT No.: PCT/EP2014/074104
§ 371 (c)(1),
(2) Date: May 3, 2016

(87) PCT Pub. No.: WO2015/067785
PCT Pub. Date: May 14, 2015

(65) Prior Publication Data
US 2016/0296448 A1    Oct. 13, 2016

(30) Foreign Application Priority Data
Nov. 8, 2013 (FR) ..................................... 13 60977

(51) Int. Cl.
| A61K 8/49 | (2006.01) |
| A61Q 5/02 | (2006.01) |
| A61Q 1/14 | (2006.01) |
| A61K 8/41 | (2006.01) |
| A61K 8/20 | (2006.01) |
| A61K 8/60 | (2006.01) |
| A61K 8/46 | (2006.01) |
| A61K 8/19 | (2006.01) |
| A61Q 19/10 | (2006.01) |
| A61K 8/44 | (2006.01) |

(52) U.S. Cl.
CPC .............. *A61K 8/4973* (2013.01); *A61K 8/19* (2013.01); *A61K 8/20* (2013.01); *A61K 8/41* (2013.01); *A61K 8/416* (2013.01); *A61K 8/44* (2013.01); *A61K 8/442* (2013.01); *A61K 8/463* (2013.01); *A61K 8/466* (2013.01); *A61K 8/602* (2013.01); *A61Q 1/14* (2013.01); *A61Q 5/02* (2013.01); *A61Q 19/10* (2013.01); *A61K 2800/592* (2013.01); *A61K 2800/596* (2013.01)

(58) Field of Classification Search
None
See application file for complete search history.

(56) References Cited

U.S. PATENT DOCUMENTS

| 4,357,141 A * | 11/1982 | Grollier | A61K 8/84 424/DIG. 2 |
| 6,716,436 B1 * | 4/2004 | Seguin | A61K 8/44 424/401 |
| 2004/0258647 A1 * | 12/2004 | Ruppert | A61K 8/463 424/70.16 |
| 2006/0197814 A1 * | 9/2006 | Doi | C09D 11/30 347/100 |
| 2012/0070396 A1 * | 3/2012 | Suzuki | A61K 8/60 424/64 |

FOREIGN PATENT DOCUMENTS

| JP | S60 31821 A | 2/1985 |
| JP | S62-030546 A | 2/1987 |
| JP | 2002-47137 A | 2/2002 |
| JP | 2006-299163 A | 11/2006 |
| KR | 10-2006-0111183 A | 10/2006 |

OTHER PUBLICATIONS

Ishigami (Ishigami, Y., et al., Surface Active Properties of Biosoap from Spiculisporic Acid, Journal of Colloid and Interface Science, 94 (1983), pp. 131-139). (Year: 1983).*
Ishigami et al., "Surface Active Properties of Biosoap from Spiculisporic Acid", Journal of Coltoid and Interface Science, vol. 94, No. 1, Jul. 1983.
M.J. Brown, "Biosurfactants for Cosmetic Applications", International Journal of Cosmetic Science 13, 61-64 (1991).
Rahman et al., "Production, Characterisation and Applications of Biosurfactants-Review", Biotechnology 7(2): 360-370, 2008.
English Abstract for KR 2006 0111183.
English Abstract for JP S60 31821.

* cited by examiner

*Primary Examiner* — Dominic Lazaro
(74) *Attorney, Agent, or Firm* — Polsinelli PC

(57) ABSTRACT

The invention relates to a cosmetic composition comprising, in a physiologically acceptable medium:
  an aqueous phase;
  spiculisporic acid;
  at least one sulfate and/or sulfonate surfactant; and
  at least one organic base;
  wherein the ratio R of the number of moles of organic base over the number of moles of spiculisporic acid is strictly greater than 1.

8 Claims, No Drawings

COSMETIC COMPOSITIONS COMPRISING SPICULISPORIC ACID AND AT LEAST ONE SULFATE AND/OR SULFONATE SURFACTANT

CROSS REFERENCE TO RELATED APPLICATIONS

This application is a National Phase filing under 35 U.S.C. § 371 of PCT/EP2014/074104 filed on Nov. 7, 2014; and this application claims priority to Application No. 1360977 filed in France on Nov. 8, 2013 under 35 U.S.C. § 119. The entire contents of each application are hereby incorporated by reference.

The present invention concerns novel stable cosmetic compositions comprising spiculisporic acid and/or one of its salts. The invention also concerns the cosmetic use of the compositions as a cleansing, hygiene and/or care product for the skin and/or for hair.

Spiculisporic acid, also known under the name of 4,5-dicarboxy-4-pentadecanolide, has the following formula:

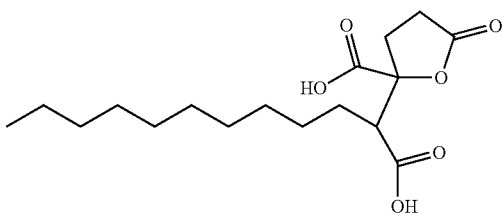 [SMILES: CCCCCCCCCCC(C(=O)O)C1(C(=O)O)CCC(=O)O1]

It is notably used as a surfactant.

From the state of the art, it is known that at room temperature, spiculisporic acid (S-acid) is insoluble in water and fats but is soluble in ethanol. Spiculisporic acid is also described as being partly soluble in water at a high temperature. At room temperature spiculisporic acid may be solubilized in water by salification. The possibility of forming three salts was shown; the sodium salts were characterized:

- S-1 Na, the monosodium salt corresponding to the product of neutralization of the carboxylic group bound to the carbon atom in position C4 of the S-acid;
- S-2Na, the disodium salt corresponding to the product of neutralization of the carboxylic groups bound to the carbon atoms in positions C4 and C5 of the S-acid;
- S-3Na, the trisodium salt corresponding to the saponification of the lactone function of S-2Na.

These salts have distinct surfactant properties. The S-1Na and S-2Na forms have surface activities suggesting a potential as surfactants.

On the other hand, and obviously, the lower the degree of salification (close to the S-1Na form), the lower is the solubility. The solubility of spiculisporic acid in water, without opening the lactone function (S-3Na form) is obtained for pH values around pH 5 to pH 7. Now, even in this optimized range, recrystallization of spiculisporic acid was observed, this being all the more significant since the temperature is low. Therefore, this is incompatible with the marketing of cosmetic products which have to be stable over time, without any recrystallization.

Therefore there exists a need for cosmetic compositions comprising spiculisporic acid and/or one of its salts, and being stable in a wide range of temperatures.

According to an embodiment, the compositions of the invention are stable at 4° C. for 15 days, more preferably 1 month, or even for two months.

Within the present application, stable compositions are compositions wherein the spiculisporic acid remains solubilized and does not recrystallize. Such compositions remain limpid over time.

The object of the present invention is to provide novel cosmetic compositions which are stable over time, based on spiculisporic acid.

Thus, the present invention relates to a cosmetic composition comprising, in a physiologically acceptable medium
- an aqueous phase;
- spiculisporic acid;
- at least one sulfate and/or sulfonate surfactant; and
- at least one organic base;

wherein the ratio R of the number of moles of organic base over the number of moles of spiculisporic acid is strictly greater than 1.

The present invention therefore relates to novel cosmetic compositions comprising the specific association of spiculisporic acid, of at least one sulfate and/or sulfonate surfactant, and of at least one organic base.

Within the scope of the invention, and unless indicated otherwise, the ratio R corresponds to the ratio of the number of moles of base over the number of moles of spiculisporic acid. Therefore this is a molar ratio. Mention may for example be made of a molar ratio R strictly greater than 1, and preferably less than or equal to 2.5. Thus, a molar ratio R strictly greater than 1 corresponds to a number of moles of base strictly greater than the number of moles of spiculisporic acid.

According to an embodiment, the ratio R is strictly greater than 1. Preferably, the ratio R is comprised between 1 and 2.5. In particular, the ratio R is equal to 2.

According to an embodiment, the ratio R is comprised between 1.1 and 2.

Surfactants

According to an embodiment, the sulfate and/or sulfonate surfactant is selected from the group consisting of sulfate and/or sulfonate anionic surfactants.

According to an embodiment, the sulfate and/or sulfonate surfactant is a sulfate anionic surfactant, a sulfonate anionic surfactant or a mixture of these surfactants.

Within the scope of the invention, and unless indicated otherwise, the term of «sulfate anionic surfactant» designates a surfactant comprising a sulfate group, i.e. an anionic surfactant comprising a —OSO$_3^-$ or —OSO$_3$H group.

According to the invention, the term of «sulfonate anionic surfactant» designates a surfactant comprising a sulfonate group, i.e. an anionic surfactant comprising a —SO$_3^-$ or —SO$_3$H group.

According to an embodiment, the sulfate anionic surfactants according to the invention are selected from the group consisting of alkyl sulfates, alkyl ether sulfates, alkyl amide ether sulfates, alkyl aryl polyether sulfates, monoglyceride-sulfates, as well as corresponding salified forms and mixtures thereof. Said alkyl groups comprise 6 to 30 carbon atoms, preferably 12 to 28 carbon atoms, more is preferably 14 to 24 carbon atoms, and even more preferably 16 to 22 carbon atoms. Said aryl group comprises 6 to 10 carbon atoms, and preferably is a phenyl or benzyl group.

These compounds may be oxyethylene compounds and then preferably include from 1 to 50 ethylene oxide units, better from 1 to 10 ethylene oxide units.

When the anionic surfactant is in the form of a salt, it may be selected from salts of alkaline metals such as a sodium or potassium salt, ammonium salt, amine salt and in particular amino alcohol salt, or a salt of earth alkaline metals such as a magnesium salt.

As an example of amino alcohol salts, mention may be made of salts of mono-, di-, and tri-ethanol amine, salts of mono-, di- or tri-isopropanol amine, salts of 2-amino 2-methyl 1-propanol, 2-amino 2-methyl 1,3-propanediol and tris(hydroxymethyl)amino methane.

Alkaline or earth alkaline metal salts are preferably used, and in particular sodium or magnesium salts.

Among sulfonate anionic surfactants, mention may in particular be made of alkylsulfonates, alkylamidesulfonates, alkylarylsulfonates, alpha-olefin sulfonates, paraffin-sulfonates, alkylsulfoacetates, N-acyltaurates, N-alkyltaurates, acylisethionates, alkylsulfolaurates, salts thereof and mixtures thereof.

Among N-alkyltaurates, mention may in particular be made of N-methyltaurates and the corresponding acid forms.

For all the aforementioned compounds, the alkyl and acyl groups preferably include from 6 to 30 carbon atoms, better from 12 to 24, or even from 16 to 22 carbon atoms, and the aryl groups are preferably a phenyl or benzyl group.

These compounds may be oxyethylened compounds and then preferably include from 1 to 50 ethylene oxide units, better from 1 to 10 ethylene oxide units.

According to an embodiment, the sulfate and/or sulfonate surfactant according to the invention is selected from the group consisting of alkylsulfates, alkylethersulfates, sulfonates, acylisethionates, N-alkyltaurates, N-acyltaurates, sulfosuccinates, alkyl sulfoacetates, and mixtures thereof.

According to the invention, the sulfate or sulfonate anionic surfactants may also be selected from alkylsulfosuccinates, alkylethersulfosuccinates, alkylamide-sulfosuccinates, and the corresponding acid forms, the alkyl groups of these compounds including from 6 to 30 carbon atoms, better from 12 to 24, or even from 16 to 22 carbon atoms.

As examples of a sulfate and/or sulfonate anionic surfactant, mention may more particularly be made of sodium lauryl sulfate, sodium laureth sulfate, sodium laurylmethyl isethionates, triethanolamine lauryl sulfate, ammonium lauryl sulfate, sodium cetostearyl sulfate, and mixtures thereof.

As sulfonates, mention may for example be made of alpha-olefin sulfonates like sodium alpha-olefin sulfonate (C14-16) marketed under the name of B10-0TERGE AS-40® by Stepan, marketed under the names of WITCONATE AOS PROTEGE® and SULFRAMINE AOS PH 12® by Witco or marketed under the name of BIO-TERGE AS-40 CG® by Stepan, the secondary sodium olefin sulfonate marketed under the name of HOSTAPUR SAS 30® by Clariant; linear alkyl aryl sulfonates like sodium xylene sulfonate marketed under the names of MANROSOL SXS30®, MANROSOL SXS40®, MANROSOL SXS93® by Manro.

As alkyl sulfoacetates, mention may be made of lauryl sulfoacetate, such as for example the one which is marketed in a mixture with sodium methyl-2-sulfolaurate and disodium sulfolaurate-2 under the reference of STEPAN MILD PCL by Stepan. Mention may also be made of the sodium lauryl sulfoacetate salt under the INCI name of SODIUM LAURYL SULFOACETATE and marketed under the name of LATHANOL LAL® by STEPAN.

As acylisethionates, mention may be made sodium cocoylisethionate, such as the product marketed under the name of JORDAPON CI P® by Jordan, as well as sodium lauroyl methyl isethionate (for example ISELUX LQ-CLR-SB from INNOSPEC).

As N-alkyl- and N-acyl-taurates, mention may be made of the sodium methyltaurate of palm kernel oil marketed under the name of HOSTAPON CT PATE® by Clariant; N-acyl N-methyltaurates like sodium N-cocoyl N-methyltaurate marketed under the name of HOSTAPON LT-SF® by Clariant or marketed under the name of NIKKOL CMT-30-T® by Nikkol, sodium palmitoyl methyltaurate marketed under the name of NIKKOL PMT® by Nikkol.

As sulfosuccinates, mention may for example be made of oxyethylene (3 EO) (C12/C14 70/30) laurylalcohol mono-sulfosuccinates marketed under the names of SETACIN 103 SPECIAL®, REWOPOL SB-FA 30 K 4® by Witco, disodium hemi-sulfosuccinate salts of C12-C14 alcohols, marketed under the name of SETACIN F SPECIAL PASTE® by Zschimmer Schwarz, oxyethylene disodium oleamidosulfosuccinate (2 EO) marketed under the name of STANDAPOL SH 135® by Cognis, oxyethylene (5 EO) lauric amide mono-sulfosuccinate marketed under the name of LEBON A-5000® by Sanyo, the disodium salt of oxyethylene (10 EO) lauryl citrate mono-sulfosuccinate marketed under the name of REWOPOL SB CS 50® by Witco, the disodium salt of lauryl alcohol mono-sulfosuccinate marketed under the name REWOPOL SB F12P® by Witco, the ricinoleic monoethanolamide mono-sulfosuccinate marketed under the name of REWODERM S 1333® by Witco. It is also possible to use polydimethylsiloxane sulfosuccinates such as disodium PEG-12 dimethicone sulfosuccinate marketed under the name of MACKANATE-DC30 by Mac Intyre.

As alkyl ether sulfates, mention may for example be made of sodium lauryl ether sulfate (CTFA name: sodium laureth sulfate) like the one marketed under the names of TEXAPON® N40 and TEXAPON® AOS 225 UP by Cognis, ammonium lauryl ether sulfate (CTFA name: ammonium laureth sulfate) like the one marketed under the name of STANDAPOL® EA-2 by Cognis, or further ammonium (C12-C14) alkyl ether (9 EO) sulfate marketed under the name of RHODAPEX AB/20® by Rhodia Chimie.

As alkyl sulfates, mention may for example be made of sodium lauryl sulfate (CTFA name: sodium lauryl sulfate) such as the product marketed by Tensachem under the name of TENSOPOL USP94, triethanolamine lauryl sulfate (CTFA name: TEA-lauryl sulfate) like the product marketed by Huntsman under the name of EMPICOL® TL40 FL or the one marketed by Cognis under the name of TEXAPON® T42, products which are at 40% in an aqueous solution. Mention may also be made of an ammonium lauryl sulfate (CTFA name: ammonium lauryl sulfate) such as the product marketed by Huntsman under the name of EMPICOL® AL 30FL which is 30% in an aqueous solution.

According to an embodiment, the sulfate and/or sulfonate surfactant is selected from the group consisting of alkyl sulfates, alkyl ether sulfates, acylisethionates and mixtures thereof.

In particular, the sulfate and/or sulfonate surfactant is selected from the group consisting of $(C_6-C_{24})$alkyl sulfates, $(C_6-C_{24})$alkyl ether sulfates comprising from 1 to 20, preferably from 2 to 10, ethylene oxide units, acylisethionates, and mixtures thereof, notably in the form of salts of alkaline metals, of ammonium, of amino alcohols, or of earth alkaline metals, or a mixture of these compounds.

In particular, $(C_{12-20})$alkyl sulfates, $(C_{12-20})$alkyl ether sulfates comprising from 1 to 20, preferably from 2 to 10, ethylene oxide units, acylisethionates, notably in the form of salts of alkaline metals, of ammonium, of amino alcohols and of earth alkaline metals, or a mixture of these compounds are preferably used.

According to an embodiment, the sulfate and/or sulfonate surfactant is selected from the group consisting of sodium lauryl sulfate, of sodium lauryl ether sulfate comprising from 2 to 10 ethylene oxide units such as the laureth sulfates marketed under the names of TEXAPON AOS 225 UP from COGNIS or IFRAPON LOS 70 RO 16 from ECOGREEN OLEOCHEMICALS, of sodium lauryl methyl isethionate and mixtures thereof.

The cosmetic compositions of the invention may comprise a single surfactant as defined above, or a mixture of surfactants as defined above.

In particular, the cosmetic compositions of the invention comprise a single sulfate and/or sulfonate surfactant. According to the invention, the total content of surfactant(s) (spiculisporic acid+additional sulfate and/or sulfonate surfactant) in the cosmetic composition of the invention may range from 0.1% to 30% by mass based on the total mass of said composition.

Preferably, the total content of surfactant(s) (spiculisporic acid+additional sulfate and/or sulfonate surfactant) according to the invention ranges from 0.5% to 15%, and preferentially from 1% to 10% by mass based on the total mass of said composition.

According to a preferred embodiment, the total content of surfactant(s) (spiculisporic acid+additional sulfate and/or sulfonate surfactant) according to the invention is comprised between 1% and 10% by mass, preferably between 3% and 8% by mass, based on the total mass of said composition.

The compositions according to the invention may also further comprise at least one additional surfactant different from the sulfate and/or sulfonate surfactants as defined above. This additional surfactant is then also different from spiculisporic acid.

According to the invention, this additional surfactant may be selected from the group consisting of amphoteric surfactants, anionic surfactants, non-ionic surfactants, cationic surfactants, and mixtures thereof.

According to an embodiment, when the compositions of the invention comprise an additional surfactant as defined above, the mass content of said additional surfactant is less than the mass content of the sulfate and/or sulfonate surfactant.

Organic Base

The compositions according to the invention comprise an organic base or a mixture of organic bases.

According to an embodiment, the organic base according to the invention is selected from the group consisting of basic amino acids, basic oligopeptides, basic amines or mixtures thereof.

The organic base may be a Bronsted-Lowry or Lewis base.

In particular, the organic base(s) may be selected from:

a) alkanoamines such as mono-, di- and tri-ethanol amines, isopropanolamine, 2-amino-2-methyl-1-propanol, b) oxyethylene and/or oxypropylene ethylenediamines, c) organic hydroxides, d) amino acids, preferably basic amino acids such as arginine, lysine, ornithine, citrulline and histidine, e) organic carbonates and bicarbonates, particularly of a primary, secondary or tertiary amine, and f) the compounds of the following formula (III):

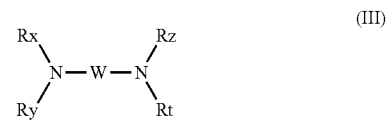

wherein W is a $C_1$-$C_6$ alkylene radical optionally substituted with a hydroxyl group or a $C_1$-$C_6$ alkyl group; Rx, Ry, Rz and Rt, either identical or different, represent a hydrogen atom, a $C_1$-$C_6$ alkyl group, a $C_1$-$C_6$ hydroxyalkyl group or a $C_1$-$C_6$ amino alkyl group.

Mention may be made as an example of such compounds of formula (III) of 1,3-diaminopropane, 1,3-diamino-2-propanol, spermine or spermidine.

The organic hydroxides are preferably selected from hydroxides of quarternary ammoniums and from guanididium hydroxide.

The hydroxide may be formed in situ such as for example guanidine hydroxide, formed by reaction of calcium hydroxide with guanidine carbonate.

The preferred alkaline agents are in particular arginine and alkanolamines.

Still better, the alkaline agent is selected from alkanolamines, in particular monoethanolamine, tri-ethanolamine, 2-amino-2-methyl-1-propanol.

Among the basic amino acids, mention may for example be made of the lysine, arginine, histidine, citrulline or ornithine.

The basic oligopeptides according to the invention are oligopeptides consisting of basic acids as defined above.

Among basic amines, mention may notably be made of monoethanolamine, diethanolamine, triethanolamine, triisopropanolamine, diisopropanolamine, monoisopropanolamine, ammonia or similar bases.

Within the scope of the present invention, it is also possible to use guanidine carbonate as an organic base.

According to an embodiment, the organic base is selected from the group consisting of arginine, triethanolamine, monoethanolamine and mixtures thereof.

Within the scope of the invention and unless indicated otherwise, the base used is a neutralizing base, i.e. it allows neutralization of spiculisporic acid in order to form a salt of said acid. Mention may for example be made of triethanolamine and arginine salts of spiculisporic acid.

According to an embodiment, the use of two moles of spiculisporic acid allows the use of two carboxylic functions of said acid without breaking the lactone function. In particular, two moles of base are used for one mole of spiculisporic acid in the aforementioned cosmetic compositions.

According to the invention, the pH of the composition according to the invention may be comprised between 4 and 10. Preferably, the pH is comprised between 5 and 8, and in particular between 5 and 6.5.

According to the invention, the spiculisporic acid content may range from 0.1% to 15% by mass based on the total mass of said composition.

According to a preferred embodiment, the spiculisporic acid content is comprised between 0.1% and 15%, preferably between 0.5% and 10%, and preferentially between 1% and 8% by mass of active material based on the total mass of the composition.

Physiologically Acceptable Medium

In addition to the compounds indicated earlier, i.e. spiculisporic acid, the organic base and the sulfate and/or sulfonate surfactant, a cosmetic composition according to the invention comprises a physiologically acceptable medium.

Within the scope of the invention, and unless indicated otherwise, by «physiologically acceptable medium» is meant a medium suitable for cosmetic applications, and notably suited to the application of a composition of the invention on the skin and/or the hair. The physiologically acceptable medium is generally adapted to the nature of the support on which the composition has to be applied, as well as to the aspect under which the composition has to be conditioned.

Aqueous Phase

The composition according to the invention comprises an aqueous phase. This aqueous phase notably comprises water and/or hydrophilic solvents like polyols.

The water used in the composition of the invention may be demineralized pure water but also mineral water and/or thermal water and/or sea water, i.e. the water of the composition may partly or completely be formed by water selected from mineral waters, thermal waters, sea waters and mixtures thereof. In general, a mineral water is consumable, which is not always the case of thermal water. Each of these waters inter alia contains solubilized minerals and/or trace elements. These waters are known so as to be used for specific treatment purposes according to the trace elements and to the particular minerals which they contain, such as hydration and desensitization of the skin or the treatment of certain dermatites. By mineral or thermal waters, are not only designated natural mineral or thermal spring waters, but also natural mineral or thermal spring waters enriched in mineral constituents and/or in additional trace elements, as well as mineral aqueous solutions and/or containing trace elements prepared from purified water (either demineralized or distilled).

A natural thermal or mineral spring water used according to the invention may for example be selected from spring water from Vittel, waters of the Vichy basin, spring water from Uriage, spring water from la Roche Posay, spring water from la Bourboule, spring water from Enghien-les-Bains, spring water from Saint Gervais-les-Bains, spring water from Néris-les-Bains, Ispring water from Allevar-les-Bains, spring water from Digne, spring water from Maizières, spring water from Neyrac-les-Bains, spring water from Lons-le-Saunier, from Eaux Bonnes, spring water from Rochefort, spring water from Saint Christau, spring water from Fumades and spring water from Tercis-les-bains, spring water from Avene.

The aqueous phase of the composition of the invention may comprise an organic solvent soluble in water at room temperature (25° C.), for example selected from lower mono-alcohols including from 2 to 6 carbon atoms and in particular 2 to 4 carbon atoms, such as ethanol, isopropanol, propanol, butanol, pentanol, hexanol, polyols with 2 to 20 carbon atoms, preferably 2 to 6 carbon atoms, like for example glycerin, propylene glycol, isoprene glycol, butylene glycol, hexylene glycol, polyethylene glycol such as PEG-8, dipropylene glycol, diethylene glycol, and mixtures thereof.

According to a preferred embodiment of the invention, the polyol is glycerin which gives better comfort to the application. It is possible to add to glycerin, other polyols insofar that the qualities of the composition are maintained.

The amount of aqueous phase is generally comprised between 60% and 100% by weight of the composition, preferably from 80% to 100% by weight, and even more preferentially from 95% to 100% by weight.

The amount of water in the aqueous phase may be greater than or equal to 10% by weight of the total weight of the composition, preferably greater than or equal to 30%, and better, greater than or equal to 50%.

Preferably, the amount of water in the composition is comprised between 50% and 95% by weight of the total weight of the composition.

The amount of polyol(s) in the aqueous phase may for example range from 0.5% to 30% by weight, preferably from 0.5% to 15% by weight. In particular, this amount may range from 1% to 10% by weight, preferably from 2% to 10% by weight and more preferentially from 2% to 8% by weight based on a total weight of the aqueous phase.

Fatty Phase

The composition according to the invention may either comprise or not a fatty phase. When it is present, the fatty phase of the composition according to the invention comprises the whole of the fat-soluble or fat-dispersible compounds present in the composition, and in particular the fats which are liquid at room temperature (25° C.) and at atmospheric pressure or oils (which form the oily phase).

The oils present in the composition according to the invention may be silicone or hydrocarbon oils.

By silicone oil, is meant oil containing at least one silicon atom, and notably containing Si-0 groups.

As silicone oils, mention may for example be made of volatile silicone oils like cyclopolydimethylsiloxanes (NCl name: cyclomethicone), such as cyclopentasiloxane, cyclohexasiloxane, octamethylcyclotetrasiloxane, decamethylcyclopentasiloxane, dodeca-methylcyclohexasiloxane; linear silicones such as heptamethylhexyl-trisiloxane, heptamehyloctyl-trisiloxane, hexamethyl-disiloxane, octamethyltrisiloxane, decamethyltetrasiloxane, dodecamethyl pentasiloxane; non-volatile silicone oils like polymethylsiloxanes (PDMS), and phenyl polymethylsiloxanes such as phenyltrimethicones, phenyldimethicones, phenyltrimethylsiloxy-diphenyl-siloxanes, diphenyl-dimethicones, diphenylmethyl-diphenyl trisiloxanes, 2-phenylethyltrimethyl-siloxysilicates, and polymethyl-phenylsiloxanes; polysiloxanes modified by fatty acids, fatty alcohols or polyoxyalkylenes and mixtures thereof.

By «volatile» is meant a compound which may evaporate in contact of the skin in less than one hour, at room temperature and at atmospheric pressure. The volatile oil is a volatile cosmetic oil, liquid at room temperature, notably having non-zero vapor pressure, at room temperature and at atmospheric pressure, in particular having a vapor pressure ranging from 0.13 Pa to 40,000 Pa ($10^{-3}$ to 300 mm Hg), and preferably ranging from 1.3 Pa to 13,000 Pa (0.01 to 100 mm Hg), and preferentially ranging from 1.3 Pa to 1,300 Pa (0.01 to 10 mm Hg).

By hydrocarbon oil, is meant an oil essentially formed, or even consisting of, carbon and hydrogen atoms, and optionally oxygen, nitrogen atoms and not containing any silicon or fluorine atom; they may contain ester, ether, amine, amide groups.

As oils which may be used in the composition of the invention, mention may for example be made of:
- hydrocarbon oils of vegetable origin, such as squalane, liquid triglycerides of fatty acids including from 4 to 30 carbon atoms like trigylcerides of heptanoic or octanoic acids or further, for example, jojoba, babassu, sunflower, olive, coconut, brazil nut, marula, maize, soya, pumpkin, grape pip, flax, sesame, hazelnut, apricot, macadamia, arara, coriander, castor, avocado oils, triglycerides of caprylic/capric acids such as those marketed by Stearineries Dubois or those marketed under the names of Miglyol 810, 812 and 818 by Dynamit Nobel, shea butter oil;
- synthetic esters and ethers notably of fatty acids, such as the oils of formulae $R^1COOR^2$ and $R^1OR^2$ in which $R^1$ represents the radical of a fatty acid or of a fatty alcohol including from 8 to 29 carbon atoms, and $R^2$ represents a hydrocarbon chain, either branched or not, containing from 3 to 30 carbon atoms, such as for example Purcelin oil, octyl-2-dodecyl stearate, octyl-2-dodecyl erucate, isostearyl isostearate; hydroxylated esters such as isostearyl lactate, octylhydroxystearate, octyldodecyl hydroxystearate, diisostearyl malate, triisocetyl citrate, heptanoates, octanoates, decanoates of fatty alcohols; polyol esters like propylene glycol dioctanoate, neopentylglycol diheptanoate and diethyleneglycol diisononanoate; and esters of pentaerythritol like pentaerythrytyl tetraisostearate;
- linear or branched hydrocarbons of mineral or synthetic origin, either volatile or non-volatile and derivatives thereof, such as branched alkanes including from 8 to 18 carbon atoms, for example $C_8$-$C_{18}$ isoalkanes (also called isoparaffins) like isododecane, isodecane, isohexadecane, such as the isoparaffins sold under the trade names of Isopar by Exxon Chemical or oils sold under the trade names Permethyl by Presperse, isohexadecane and isododecane marketed by INEOS; as well as Vaseline oil and hydrogenated polyisobutene such as Parléam® oil marketed by Nof Corporation; volatile linear alkanes comprising from 7 to 17 carbon atoms like undecane, tridecane such as the one described in examples 1 and 2 of patent application WO2008/155059 of Cognis;
- fatty alcohols liquid at room temperature having from 8 to 26 carbon atoms, preferably 12 to 18 carbon atoms such as octyldodecanol, 2-butyloctanol, 2-hexyldecanol, 2-undecylpentadecanol or oleic alcohol; and
- mixtures thereof.

Mention may in particular be made of the following oils:
- esters derived from the reaction of at least one fatty acid including at least 6 carbon atoms, preferably from 6 to 26 carbon atoms and better from 6 to 20 carbon atoms, still better from 6 to 16 carbon atoms and of at least one alcohol comprising from 1 to 17 carbon atoms and better from 3 to 15 carbon atoms; mention may notably be made of isopropyl myristate, isopropyl palmitate, ethyl-2-hexyl caprate/caprylate (or octyl caprate/caprylate), ethyl-2-hexyl palmitate, isostearyl neopentanoate, isononyl isononanoate, hexyl laurate, lactic acid esters with fatty acids comprising 12 or 13 carbon atoms, dicaprylyl carbonate like the one which is marketed under the name of CETIOL CC by COGNIS,
- fatty acid ethers comprising from 6 to 20 carbon atoms such as dicaprylyl ether (as the one sold under the trade name Cetiol OE from Cognis),
- glycerol ethers comprising from 6 to 12 carbon atoms like 2-ethyl hexyl ether glycerol (INCI name: ethylhexylglycerin) such as Sensiva SC 50 from Schulke & Mayr GmbH;
- octyldodecanol,
- alkanes such as those which are described in patent applications of Cognis, WO 2007/068371, or WO2008/155059 (mixtures of distinct alkanes, different by at least one carbon). These alkanes are obtained from fatty alcohols, themselves obtained from coconut or palm oil.

As an example of linear alkanes suitable for the invention, mention may be made of n-heptane (C7), n-octane (C8), n-nonane (C9), n-decane (C0), n-undecane (C11), n-dodecane (C12), n-tridecane (C13), n-tetradecane (C14), and mixtures thereof. According to a particular embodiment, the volatile linear alkane is selected from n-nonane, n-undecane, n-dodecane, n-tridecane, n-tetradecane, and mixtures thereof.

According to a preferred embodiment, mention may be made of the mixtures of n-undecane (C11) and of n-tridecane (C13) obtained in Examples 1 and 2 of the WO2008/155059 application of Cognis;
- the polyesters obtained by condensation of an unsaturated fatty acid dimer and/or trimer and of a diol such as for example the polyesters of dilinoleic acid and of a diol marketed by Biosynthis under the name of Viscoplast and notably the polymer bearing the INCI name: dilinoleic acid/propanediol copolymer; and
- mixtures thereof.

Preferably, the oil is selected from vegetable oils as mentioned above.

The amount of fatty phase in the composition of the invention may range from 0% to 40% by weight, preferably from 0.1% to 20% by weight based on a total weight of the composition.

According to a particular embodiment of the invention, the amount of fatty phase in the composition is comprised between 0% and 5% by weight of the total weight of the composition.

Additives

A cosmetic composition according to the invention may also further comprise any additive customarily used in the relevant field, for example, selected from gums, resins, dispersants, semi-crystalline polymers, anti-oxidants, essential oils, preservatives, perfumes, neutralizers, antiseptic agents, UV protective agents, cosmetic actives, such as vitamins, moisturizing agents, emollients or collagen protective agents, and mixtures thereof.

The adjustment of the nature and of the amount of the additives present in the composition according to the invention falls under routine operations of one skilled in the art, so that the cosmetic properties and the desired stability properties of the latter are not affected by this.

Preparation of the Composition

According to an embodiment, the cosmetic composition according to the invention is prepared according to the following steps:
- step a): preparation of an aqueous solution A of spiculisporic acid with an organic base;
- optional step b): heating the aforementioned aqueous solution A;
- step c): adding at least one aforementioned sulfate and/or sulfonate surfactant to the solution A at the end of step b) in order to lead to a solution B; and then
- step d): adding an organic phase miscible with water to the solution B.

According to an embodiment, the solution A comprises a salt of spiculisporic acid, synthesized from spiculisporic acid and from an organic base selected from triethanolamine and L-arginine.

According to an embodiment, the cosmetic composition according to the invention is prepared according to the following steps:
- step a) : preparing an aqueous solution A of spiculisporic acid with an organic base;
- step b): heating the aforementioned aqueous solution A;
- step c): adding at least one aforementioned sulfate and/or sulfonate surfactant to the solution A at the end of step b) in order to lead to a solution B; and then
- step d): adding an organic phase miscible with water to the solution B.

According to an embodiment, step b) consists in heating the aqueous solution A to a temperature comprised from 30° C. to 90° C., preferably from 35° C. to 60° C., and preferentially to a temperature of about 40° C. This step advantageously allows acceleration of the solubility.

According to an embodiment, the solution B obtained at the end of step c) comprises water, spiculisporic acid in a salified form, and at least one surfactant according to the invention.

According to an embodiment, the organic phase miscible with water added to the solution B comprises at least one organic solvent as mentioned above.

Uses

The cosmetic composition according to the invention may be care, sun protective, cleansing (removing makeup) or hygiene products for skin and/or hair.

These compositions are therefore intended to be applied on the skin and/or on is the hair.

Thus, the present invention also relates to the non-therapeutic cosmetic use of the aforementioned cosmetic composition, as a hygiene, cleansing and/or care product for skin and/or hair.

According to an embodiment, the compositions of the invention are in the form of a make-up removal agent, a care product for the face and/or the body and/or the hair, an anti-ageing care product, a sunscreen, a fatty skin care product, a whitening care product, a moisturizing care product, a hair conditioning care product, a face and/or body cleansing agent, a shower gel or a shampoo.

In particular, the compositions of the invention are used in foaming products for hygiene of the face, of the body and of the hair.

The present invention also relates to a non-therapeutic cosmetic method for hygiene, cleansing and/or care of the skin and/or of the hair comprising a step for applying on the skin at least one layer of a cosmetic composition according to the invention.

In all the application, the expression «comprising one» or «including one» means «comprising at least one» or «including at least one», i.e. «comprising one or more» or «including one or more», unless specified otherwise.

In all the description above, unless mentioned otherwise, the term of «comprised between x and y» corresponds to an inclusive range, i.e. the values x and y are included in the range.

The invention will be illustrated in the following non-limiting examples. Unless indicated otherwise, the percent are expressed by weight based on the total weight of the composition.

The compositions are prepared according to the customary methods for formulating cosmetic compositions.

EXAMPLES

It has been advantageously shown that the cosmetic compositions according to the invention are stable in a wide temperature range. This is notably related to the association of spiculisporic acid and of an organic base with at least one sulfate and/or sulfonate surfactant, and with a minimum salification level such that a base is present at a molar ratio R (base:spiculisporic acid) strictly greater than 1 and preferentially less than or equal to 2.5.

Raw Material: Spiculisporic Acid
Supplier: Iwata Chemical

Example 1

Salification of Spiculisporic Acid

Different salification levels of spiculisporic acid (S-acid) were evaluated. For this, tests were conducted with molar ratios between the neutralizing base and the S-acid selected so that R (ratio as defined above) is strictly greater than 1.

It was observed that compositions with a ratio $R \leq 2$ are particularly advantageous in that they allow working under pH conditions compatible with the majority of cosmetic products and optimal conditions for the activity of the S-acid (maintaining the lactone function).

The amount of base for neutralizing the S-acid, according to the selected ratio R, was defined as:

$$mass_{(base)} \text{g} = 2 \times \frac{mass_{(S\text{-}acid)} \text{g}}{MM_{(S\text{-}acid)} \text{g} \cdot \text{mol}^{-1}} \times MM_{(base)} \text{g} \cdot \text{mol}^{-1}$$

The molar masses used are given in the following table:

|  | Molecular formula | Molar mass (g · mol$^{-1}$) |
| --- | --- | --- |
| S-acid | $C_{17}H_{28}O_6$ | 328.4 |
| Sodium hydroxide | NaOH | 40 |
| Potassium hydroxide | KOH | 56.1 |
| Triethanolamine (TEA) | $C_6H_{15}NO_3$ | 149.19 |
| L-arginine | $C_6H_{14}N_4O_2$ | 174.2 |

Example 2

Demonstrating the Incompatibility of the S-Acid with Sulfate Surfactants and Sulfonate Surfactants Solutions containing the S-acid at 4% or 8% (neutralized with an amount of KOH calculated so as to obtain the di-potassium salt of S-acid, i.e. $R_1=2$) and surfactants, were made.

TABLE 1

Aspects and pH values of the solutions of spiculisporic acid pre-solubilized with KOH in association with different families of surfactants.

| Name | Classification | compound (% of active material) | Acid S (% MA) | pH t0 RT | 20 days after storage pH RT | 20 days after storage pH T = 4° C. |
|---|---|---|---|---|---|---|
| S-acid alone | Anionic | — | 8 | 6.43 | 6.47 | 6.47* |
| S-acid alone | anionic | — | 4 | 5.97 | 6.02 | 6.01* |
| Acid/surfactant associations | | | | | | |
| Lauryl betaïne (and) sodium chloride (sold under the name empigen BB/LS by Huntsman) | amphoteric | 4 | 4 | 7.06 | 7 | 7.06 |
| Cocamidopropylbetaïne (sold under the name Empigen Total Active TC/U by Huntsman) | amphoteric | 4 | 4 | 7.03 | 6.93 | 7 |
| Disodiumcocoamphodiacetate (sold under the name Miranol C2M conc NP by Rhodia) | amphoteric | 4 | 4 | 7.88 | 7.98 | 8.12 |
| coco-glucoside (sold under the name plantacare 818 UP by cognis) | non-ionic | 4 | 4 | 6.67 | 6.72 | 6.72 |
| decyl glucoside (sold under the name Plantacare 2000 UP by Cognis) | non-ionic | 4 | 4 | 6.91 | 6.92 | 6.99 |
| sucrose laurate (and) sorbitol (sold under the name Napture O gel V by sensient) | non-ionic | 4 | 4 | 6.45 | 6.46 | 6.48 |
| disodium cocoyl glutamate (sold under the name Plantapon ACG HC by cognis) | anionic | 4 | 4 | 8.3 | 7.68 | 8.29 |
| Sodium lauryl sarcosinate (sold under the name Sarkosyl NL 97 by Ciba Geigy) | anionic | 4 | 4 | 6.82 | 6.88 | 6.88 |
| Comparative examples | | | | | | |
| Sodium lauryl sulfate (sold under the name Tensopol A 795 by Tensachem) | anionic | 4 | 4 | 7.05* | 6.51* | 6.52* |
| Sodium lauryl methyl isethionate (sold under the name Iselux by Innospec Active Chemicals) | anionic | 4 | 4 | 6.38 | 6.44 | 6.46* |

Macroscopic observation gave the possibility of showing that the solution marked as (*) exhibited a precipitate, the other solutions being limpid.

The results of Table 1 showed after 20 days of storage at 4° C.:
precipitation of the S-acid alone at 4% and 8%;
precipitation of the associations with sulfate anionic surfactants and sulfonate anionic surfactants: sodium lauryl sulfate and sodium isethionate.
These results show that:
The S-acid solubilized in an aqueous solution recrystallizes under stability conditions required for the cosmetic products (4° C.);
The association with specific surfactants gives the possibility of clearly improving the stability of the solubility of the S-acid under unfavorable temperature conditions (4° C.) compatible with the cosmetic products; and
The sulfate and/or sulfonate surfactants do not give the possibility of avoiding recrystallization when the S-acid is salified by metal bases (KOH, NaOH).

Example 3

Demonstration of a Technical Solution giving the Possibility of Associating the S-Acid with Sulfate and/or Sulfonate Surfactants by using Organic Bases Solutions, associating the S-acid at 4%, neutralized by the organic bases, arginine (Arg) or triethanolamine (TEA), and a sulfate surfactant (sodium lauryl sulfate) (SLS) or a sulfonate surfactant (sodium lauryl methyl isethionate) were made.

TABLE 2

Aspects and pH values of the solutions of S-acid salified with the KOH, Arg or TEA bases under neutralization conditions such as $1.1 \leq R \leq 2$

| Sulfate surfactant % MA | Sulfonate surfactant % MA | S-acid % MA | base | R | 24 h RT | 15 days RT | 15 days 4° C. |
|---|---|---|---|---|---|---|---|
| 4.00 | | 4.00 | KOH | 2.00 | x | 6.33* | 6.24* |
| | 4.00 | 4.00 | KOH | 2.00 | x | 6.43 | 6.34* |
| 4.00 | | 4.00 | Arg | 2.00 | x | 6.21 | 6.25 |
| | 4.00 | 4.00 | Arg | 2.00 | x | 6.18 | 6.19 |
| 4.00 | | 4.00 | TEA | 2.00 | x | 6.32 | 6.32 |
| | 4.00 | 4.00 | TEA | 2.00 | x | 6.33 | 6.34 |
| 4.00 | | 4.00 | Arg | 1.75 | x | 5.95 | 5.93 |
| | 4.00 | 4.00 | Arg | 1.75 | x | 5.93 | 5.89 |
| 4.00 | | 4.00 | TEA | 1.75 | x | 5.98 | 6.02 |
| | 4.00 | 4.00 | TEA | 1.75 | x | 5.97 | 5.96 |
| 4.00 | | 4.00 | Arg | 1.25 | x | 5.34 | 5.33 |
| | 4.00 | 4.00 | Arg | 1.25 | x | 5.27 | 5.28 |
| 4.00 | | 4.00 | TEA | 1.25 | x | 5.39 | 5.38 |
| | 4.00 | 4.00 | TEA | 1.25 | x | 5.33 | 5.37 |

TABLE 2-continued

Aspects and pH values of the solutions of S-acid salified with the KOH, Arg or TEA bases under neutralization conditions such as $1.1 \leq R \leq 2$

| Sulfate surfactant % MA | Sulfonate surfactant % MA | S-acid % MA | base | R | 24 h RT | 15 days RT | 4° C. |
|---|---|---|---|---|---|---|---|
| 4.00 | | 4.00 | Arg | 1.10 | x | 5.11 | 5.19 |
| | 4.00 | 4.00 | Arg | 1.10 | x | 5.00 | 5.07 |
| 4.00 | | 4.00 | TEA | 1.10 | x | 5.19 | 5.26 |
| | 4.00 | 4.00 | TEA | 1.10 | x | 5.17 | 5.22 |

Macroscopic observation gave the possibility of demonstrating that the solution marked with (*) showed a precipitate, the other solutions being limpid.

These results:
confirm the incompatibility of the S-acid salified with a metal base, here KOH, with sulfate and sulfonate surfactants;
show that the use of the organic bases, arginine and TEA, give the possibility of keeping solutions limpid both after 15 days at room temperature or at 4° C., an unfavorable temperature.

As a conclusion, the salification of the S-acid specifically with organic bases gives the possibility of associating spiculisporic acid with sulfate surfactants and with sulfonate surfactants, under conditions compatible with cosmetic products and unfavorable temperatures (4° C.).

This opens the route to the use of S-acid with sulfate surfactants and sulfonate surfactants, widely used in cosmetics.

TABLE 3

Examples of association formulations of different salts of spiculisporic acid associated with a sulfate surfactant and a sulfonate surfactant.

| | INCI | 1 | 2 | 3 | 4 | 5 | 6 | 7 | 8 | 9 | 10 |
|---|---|---|---|---|---|---|---|---|---|---|---|
| Phase A | Water | 88.47 | 88.77 | 86.96 | 87.26 | 87.57 | 87.87 | 87.49 | 87.79 | 88.02 | 88.32 |
| | spiculisporic acid (100% MA) | 4.00 | 4.00 | 4.00 | 4.00 | 4.00 | 4.00 | 4.00 | 4.00 | 4.00 | 4.00 |
| | potassium hydroxide (50% MA) | 2.73* | 2.73* | | | | | | | | |
| | arginine (100% MA) | | | 4.24 | 4.24 | | | 3.71 | 3.71 | | |
| | triethanolamine (100% MA) | | | | | 3.63 | 3.63 | | | 3.18 | 3.18 |
| Phase B | sodium lauryl sulfate (93% MA) (sold under the name Tensopol A 795 by Tensachem) | 4.30 | | 4.30 | | 4.30 | | 4.30 | | 4.30 | |
| | sodium lauryl methyl isethionate (100% MA) (sold under the name Iselux by Innospec Active Chemicals) | | 4.00 | | 4.00 | | 4.00 | | 4.00 | | 4.00 |
| Phase C | phenoxyethanol (and) methylparaben (and) ethylparaben (and) propylparaben (and) isobutylparaben (and) butylparaben | 0.50 | 0.50 | 0.50 | 0.50 | 0.50 | 0.50 | 0.50 | 0.50 | 0.50 | 0.50 |
| | Total | 100.00 | 100.00 | 100.00 | 100.00 | 100.00 | 100.00 | 100.00 | 100.00 | 100.00 | 100.00 |
| | R | 2.00 | 2.00 | 2.00 | 2.00 | 2.00 | 2.00 | 1.75 | 1.75 | 1.75 | 1.75 |

| | INCI | 11 | 12 | 13 | 14 | 15 | 16 | 17 | 18 |
|---|---|---|---|---|---|---|---|---|---|
| Phase A | Water | 88.55 | 88.85 | 88.93 | 89.23 | 88.87 | 89.17 | 89.20 | 89.50 |
| | spiculisporic acid (100% MA) | 4.00 | 4.00 | 4.00 | 4.00 | 4.00 | 4.00 | 4.00 | 4.00 |
| | potassium hydroxide (50% MA) | | | | | | | | |
| | arginine (100% MA) | 2.65 | 2.65 | | | 2.33 | 2.33 | | |
| | triethanolamine (100% MA) | | | 2.27 | 2.27 | | | 2.00 | 2.00 |
| Phase B | sodium lauryl sulfate (93% MA) (sold under the name Tensopol A 795 by Tensachem) | 4.30 | | 4.30 | | 4.30 | | 4.30 | |
| | sodium lauryl methyl isethionate (100% MA) (sold under the name Iselux by Innospec Active Chemicals) | | 4.00 | | 4.00 | | 4.00 | | 4.00 |
| Phase C | phenoxyethanol (and) methylparaben (and) ethylparaben (and) propylparaben (and) | 0.50 | 0.50 | 0.50 | 0.50 | 0.50 | 0.50 | 0.50 | 0.50 |

TABLE 3-continued

Examples of association formulations of different salts of spiculisporic acid associated with a sulfate surfactant and a sulfonate surfactant.

| | | | | | | | | |
|---|---|---|---|---|---|---|---|---|
| isobutylparaben (and) butylparaben | | | | | | | | |
| Total | 100.00 | 100.00 | 100.00 | 100.00 | 100.00 | 100.00 | 100.00 | 100.00 |
| R | 1.25 | 1.25 | 1.25 | 1.25 | 1.10 | 1.10 | 1.10 | 1.10 |

The compositions of Table 3 above were prepared according to the following operating procedure:

Phase A was heated to 40° C. After solubilization of the S-acid, the phase B was added to the Phase A. Next, the phase C was added after phase B.

A portion of the solution was stored at room temperature and the other one at 4° C.

Macroscopic observation gave the possibility of showing that the solution marked with (*) exhibited a precipitate, the other solutions being limpid.

These results confirm the incompatibility of KOH with sulfate and sulfonate surfactants, whereas organic bases like arginine and triethanolamine afford stable solutions of spiculisporic acid, according to the invention.

Example 4

Demonstration of a Technical Solution giving the Possibility of is Associating the S-Acid with Sulfate and/or Sulfonate Surfactants by using Organic Bases Solutions, associating the S-acid at 4%, neutralized by the organic bases, arginine (Arg) or monoethanolamine (MEA), and a sulfate surfactant (sodium lauryl sulfate (SLS)); or a sulfonate surfactant (sodium methyl cocoyl taurate and sodium lauryl sulfoacetate) were made.

The compositions were prepared according to the following procedure:

The S-spiculisporic acid aqueous solutions are prepared, then the required amount of base is added and the resulting solution is stirred at 40° C. The surfactant is then added.

The solutions are stored for 12 days at room temperature or in the darkness at 4° C. The appearance of the composition is observed (presence of precipitate or limpid solution).

| INCI name | S-acid % MA | Base | R | surfactant % MA | pH t0 RT | 12 days at RT | 12 days at 4° C. |
|---|---|---|---|---|---|---|---|
| SLS (93% MA) (Tensopol A 795 from Tensachem | 4.0 | KOH | 1.1 | 4.0 | 5.2 | L | P |
| Sodium Methyl Cocoyl Taurate (30% MA) (HOSTAPON CT PATE from Clariant) | 4.0 | KOH | 1.1 | 4.0 | 5.26 | L | P |
| Sodium Lauryl Sulfoacetate (65% MA) (LATHANOL LAL POWDER from Stepan Europe) | 4.0 | KOH | 1.1 | 4.0 | 5.05 | L | P |
| SLS (93% MA) (Tensopol A 795 from Tensachem | 4.0 | KOH | 2 | 4.0 | 7.55 (P) | P | P |
| Sodium Methyl Cocoyl Taurate (30% MA) (HOSTAPON CT PATE from Clariant) | 4.0 | KOH | 2 | 4.0 | 7.62 | L | P |
| Sodium Lauryl Sulfoacetate (65% MA) (LATHANOL LAL POWDER from Stepan Europe) | 4.0 | KOH | 2 | 4.0 | 7.19 (P) | P | P |
| SLS (93% MA) (Tensopol A 795 from Tensachem | 4.0 | MEA | 1.1 | 4.0 | 5.09 | L | L |
| Sodium Methyl Cocoyl Taurate (30% MA) (HOSTAPON CT PATE from Clariant) | 4.0 | MEA | 1.1 | 4.0 | 5.17 | L | L |
| Sodium Lauryl Sulfoacetate (65% MA) (LATHANOL LAL POWDER from Stepan Europe) | 4.0 | MEA | 1.1 | 4.0 | 4.96 | L | L |
| SLS (93% MA) (Tensopol A 795 from Tensachem | 4.0 | MEA | 2 | 4.0 | 7.85 | L | L |
| Sodium Methyl Cocoyl Taurate (30% MA) (HOSTAPON CT PATE from Clariant) | 4.0 | MEA | 2 | 4.0 | 7.44 | L | L |
| Sodium Lauryl Sulfoacetate (65% MA) (LATHANOL LAL POWDER from Stepan Europe) | 4.0 | MEA | 2 | 4.0 | 7.26 | L | L |
| SLS (93% MA) (Tensopol A 795 from Tensachem | 4.0 | Arg | 1.1 | 4.0 | 5.11 | L | L |
| Sodium Methyl Cocoyl Taurate (30% MA) (HOSTAPON CT PATE from Clariant) | 4.0 | Arg | 1.1 | 4.0 | 5.11 | L | L |

-continued

| INCI name | S-acid % MA | Base | R | surfactant % MA | pH t0 RT | 12 days at RT | 12 days at 4° C. |
|---|---|---|---|---|---|---|---|
| Sodium Lauryl Sulfoacetate (65% MA) (LATHANOL LAL POWDER from Stepan Europe) | 4.0 | Arg | 1.1 | 4.0 | 4.95 | L | L |
| SLS (93% MA) (Tensopol A 795 from Tensachem | 4.0 | Arg | 2 | 4.0 | 7.43 | L | L |
| Sodium Methyl Cocoyl Jaurate (30% MA) (HOSTAPON CT PATE from Clariant) | 4.0 | Arg | 2 | 4.0 | 7.12 | L | L |
| Sodium Lauryl Sulfoacetate (65% MA) (LATHANOL LAL POWDER from Stepan Europe) | 4.0 | Arg | 2 | 4.0 | 7.19 | L | L |

In this table, P means that a precipitate is observed in the composition, and L means that a limpid solution is observed.

These results show again:

the presence of a precipitate while using a mineral base (KOH) in presence of sulfate or sulfonate surfactants;

limpid solutions while using organic base (MEA or arginine) in presence of sulfate or sulfonate base.

Importantly, the results follow the same trend, independently from R (1.1 or 2).

These results confirm the incompatibility of a mineral base like KOH with sulfate and sulfonate surfactants to stabilize S-spiculisporic acid in aqueous solution, whereas organic bases like arginine and monoethanolamine afford stable solutions of spiculisporic acid, according to the invention.

The invention claimed is:

1. A cosmetic composition comprising, in a physiologically acceptable medium:
   an aqueous phase:
   spiculisporic acid;
   at least one sulfate and/or sulfonate surfactant selected from the group consisting of alkylsulfates, alkylethersulfates, alkylsulfonates, alkylamidesulfonates, alkylarylsulfonates, alpha-olefin-sulfonates, paraffin-sulfonates, acylisethionates, N-alkyltaurates, N-acyltaurates, sulfosuccinates, alkyl sulfoacetates, and mixtures thereof; and
   at least one organic base selected from the group consisting of basic amino acids, basic oligopeptides, basic amines and mixtures thereof;
   wherein spiculisporic acid is present in a content ranging from 0.1% to 15% by mass based on the total mass of said composition;
   wherein the total content of the at least one sulfate and/or sulfonate surfactant ranges from 0.1% to 30% by mass based on the total mass of said composition;
   wherein the ratio R of the number of moles of organic base over the number of moles of spiculisporic acid is between 1.1 and 2.

2. The cosmetic composition according to claim 1, wherein the ratio R is equal to 2.

3. The cosmetic composition according to claim 1, wherein the sulfate and/or sulfonate surfactant is selected from the group consisting of alkylsulfates, alkylethersulfates, acylisethionates, and mixtures thereof.

4. The cosmetic composition according to claim 1, wherein the sulfate and/or sulfonate surfactant is selected from the group consisting of sodium lauryl sulfate, sodium lauryl ether sulfate comprising from 2 to 10 ethylene oxide units, sodium lauryl methyl isethionate and mixtures thereof.

5. The cosmetic composition according to claim 1, wherein the organic base is selected from the group consisting of arginine, triethanolamine and mixtures thereof.

6. The non therapeutic cosmetic use of a cosmetic composition according to claim 1, wherein the composition is used as a hygiene product, cleansing product, and/or care product for the skin and/or for the hair.

7. A non-therapeutic hygiene, cleansing and/or care cosmetic method for the skin and/or the hair, comprising a step for applying on the skin at least one layer of a composition according to claim 1.

8. A cosmetic composition comprising, in a physiologically acceptable medium:
   an aqueous phase:
   spiculisporic acid;
   at least one sulfate and/or sulfonate surfactant selected from the group consisting of alkylsulfates, acylisethionates, N-alkyltaurates, N-acyltaurates, alkyl sulfoacetates and mixtures thereof; and
   at least one organic base selected from the group consisting of basic amino acids, basic oligopeptides, basic amines and mixtures thereof;
   wherein spiculisporic acid is present in a content ranging from 0.1% to 15% by mass based on the total mass of said composition;
   wherein the total content of the at least one sulfate and/or sulfonate surfactant ranges from 0.1% to 30% by mass based on the total mass of said composition;
   wherein the ratio R of the number of moles of organic base over the number of moles of spiculisporic acid is between 1.1 and 2.

* * * * *